United States Patent [19]
Amouyel et al.

[11] Patent Number: 5,942,392
[45] Date of Patent: Aug. 24, 1999

[54] GENETIC MARKERS USED JOINTLY FOR THE DIAGNOSIS OF ALZHEIMER'S DISEASE, AND DIAGNOSTIC METHOD AND KIT

[75] Inventors: Philippe Amouyel, Marcq En Baroeul; Marie-Christine Chartier-Harlin, Villeneuve D'Aso, both of France

[73] Assignees: Institut Pasteur de Lille, Lille Cedex; Institut National de la Sante et de la Recherche Medicale, Paris Cedex, both of France

[21] Appl. No.: 08/702,548

[22] PCT Filed: Mar. 6, 1995

[86] PCT No.: PCT/FR95/00259

§ 371 Date: Jan. 2, 1997

§ 102(e) Date: Jan. 2, 1997

[87] PCT Pub. No.: WO95/24504

PCT Pub. Date: Sep. 15, 1995

[30] Foreign Application Priority Data

Mar. 7, 1994 [FR] France .................................. 94 02603

[51] Int. Cl.$^6$ ............................. C12Q 1/68; C07H 21/04
[52] U.S. Cl. ............................. 435/6; 435/975; 536/24.3; 536/24.31; 536/24.33; 536/25.3
[58] Field of Search ............................. 435/6, 975, 91.2, 435/91.1, 91.5, 91.4; 436/808, 71; 536/23.1, 23.5, 24.3, 24.31, 24.33, 25.3

[56] References Cited

PUBLICATIONS

Aldrich Chemical Company Incorp. pages.
Lebo et al, Cold Spring Harbor Symposium on Quantitative Biology, vol. LI pp. 169–176. 1986.
McConkey, in Human Genomics: The Molecular Revolution by Tones & Bartlett Publishers, Boston 1993 pp.50–63.
McKhana et al., Neurology, 34: 939–944, 1984.
Warner, M., Analytical Chemistry 59(20) :1023–1024, 1987.
Lidell et al, Journal of Medical Genetics 31(3) : 197–200, 1994 See Abstract.
Tsuda et al, Animals of Neurology 36(1):97–100, 1994.
W.M. Nillesen et al., "Human ApoCI Hpal Restriction Site Polymorphism Revealed by the Polymerase Chain Reaction", Nucleic Acids Research, vol. 18, No. 11, p. 3428.
James E. Hixon et al., "Restriction Isotyping of Human Apolipoprotein E by Gene Amplification and Cleavage with HhaI", Journal of Lipid Research, vol 31, pp. 545–548, 1990.
Annals of Neurology, vol. 31. No. 2, Feb. 1992, Lissle, Brown and Company, Boston, MA. US; pp. 223–227.
Neurology, vol. 43, No. 8, Aug. 1993, Edgell Communication Inc., Duluth, Minn. US; pp. 1467–1472.
Science, vol. 261, Aug. 13, 1993, AAAS, Washington, DC. US; pp. 921–923.
Proceedings of the National Academy of Sciences, vol. 90, No. 5, Mar. 1, 1993, National Academy of Science, Washington, DC. US; pp. 1977 –1981.
Human Genetics, vol. 44, No. 3, Mar. 1989, American Society of Human Genetics, University of Chicago Press, US; pp. 338–396.
Cytogenetics and Cell Genetics, vol. 58, No. 1–4, 1991, Karger, New York, US; pp. 751–784.
Human Molecular Genetics, vol. 3, No. 4, Apr. 1994, Oxford University Press, Cambridge, UK; pp. 569–574.

*Primary Examiner*—Patricia A. Duffy
*Attorney, Agent, or Firm*—Oblon, Spivak, McClelland, Maier & Neustadt, P.C.

[57] ABSTRACT

Combined use of at least two genetic markers selected from apolipoprotein E, D19S178 and apolipoprotein CII, for the diagnosis of Alzheimer's disease, especially apolipoprotein $\epsilon4$, long apolipoprotein CII ($30\pm3$ repeat patterns (CA) and short D19S178 (less than $167\pm4$ nucleotides) alleles. The invention also concerns a method for the diagnosis of Alzheimer's disease and a kit for carrying out said method.

26 Claims, No Drawings

GENETIC MARKERS USED JOINTLY FOR THE DIAGNOSIS OF ALZHEIMER'S DISEASE, AND DIAGNOSTIC METHOD AND KIT

The present invention relates to genetic markers used jointly for the diagnosis of Alzheimer's disease.

Alzheimer's disease is a brain pathology characterized by an early dementia with a loss of cortical neurons associated with plaques of β-amyloid, neurofibrillary tangles and, in most cases, an amyloid angiopathy. It is strongly suspected that there is a genetic influence in the aetiology of Alzheimer's disease (WO 94/01772).

This genetic component has been brought to the fore over many years by indirect observations which suggest that the disease is inherited in autosomal dominant fashion with an age-dependant penetrance in order to explain the family links between individuals suffering from the disease. Recent molecular genetic studies have enabled putative genes for Alzheimer's disease to be isolated by looking for chromosome-specific polymorphic genetic markers (Bird et al., 1989, Neurobiology of Aging 10, 432–434).

Three chromosomal localizations have been described as being involved in the early onset familial forms (age at onset under 60 years): chromosome 21, chromosome 14 and chromosome 19. Two linkage studies have suggested that the chromosomal region 19q13.2 was associated with late onset familial forms of Alzheimer's disease (Pericak-Vance et al., Am. J. Hum. Genet. (1991), 48, 1034–1050; Schellenberg et al., Ann. Neurol. (1992), 31, 223–227). Within this chromosomal region, the group of genes for apolipoproteins (APO) E-CI-CI'-CII is a candidate zone. Among the products of these genes, apolipoprotein E (APOE) is involved especially in the nervous system: APOE is present in the senile plaques and possesses a binding affinity for the peptide β-A4. Strittmatter et al. (Proc. Natl. Acad. Sci. (1993) 90, 177–181) have described an increased frequency of the ε4 allele of the APOE gene in the late onset familial forms of Alzheimer's disease. This observation has been confirmed for the familial forms (Corder et al., Science (1993), 261, 921–923) and the sporadic forms of Alzheimer's disease (Corder et al., Science (1993), 261, 921–923; Saunders et al., Neurology (1993), 13, 1467–1472).

Moreover, Schellenberg et al. (Ann. Neurol. 1992, 31: 223–227) have reported a genetic association between the F allele of the apolipoprotein CII gene (TaqI restriction fragment length polymorphism (RFLP) allele) and the familial form of Alzheimer's disease.

The authors of the present invention have carried out a study covering two populations of different origins, one suffering from a late onset form of Alzheimer's disease (after 65 years) and the other from an early onset form of Alzheimer's disease (before 65 years), which permitted a significant increase to be established in both groups of at least two of the following genetic markers: APOE ε4 allele, short D19S178 allele and long APO CII allele.

The localization of the APOE, APO CII (APO C2) and D19S178 markers on chromosome 19 is known and described, in particular, by Williamson et al. (Cyto Genetic and Cell Genetic 1991, vol. 58, p. 1678).

Thus the subject of the present invention is the joint use of at least two genetic markers selected from APOE, D19S178 and APO CII for the diagnosis of Alzheimer's disease, the genetic markers preferably consisting of APOE and D19S178 and/or APO CII, and as a further preference APOE, D19S178 and APO CII.

The genetic markers used are advantageously the APOE ε4 allele, the short D19S178 allele and the long APO CII allele.

The APOE gene possesses three alleles: ε2, ε3 and ε4.

Long APO CII allele is understood to mean an allele comprising more than 30±3, and preferably more than 30, consecutive repeats of the bases cytosine-adenine.

Short D19S178 allele is understood to mean an allele comprising fewer than 167±4, and preferably fewer than 167, nucleotides.

The subject of the invention is also a method of diagnosis of Alzheimer's disease, characterized in that the presence of at least two of the following markers is tested for in a biological sample from a patient: APOE ε4 allele, short D19S178 allele and long APO CII allele.

The method according to the invention advantageously comprises the following steps:

a) bringing of the biological sample containing DNA into contact with a pair of specific primers permitting the amplification of all or part of the APOE, D19S178 and/or APO CII genes, the human DNA contained in the sample having been rendered accessible, where appropriate, to hybridization, and under conditions permitting a hybridization of the primers with the human DNA contained in the biological sample;

b) amplification of the human DNA;

c) visualization of the amplification products by suitable techniques;

d) detection of the possible presence of the APOE ε4, short D19S178 and long APO CII alleles by suitable techniques.

For the purposes of the present invention, diagnosis is understood to mean the confirmation of the presence of at least two markers selected from those described above in patients whose clinical picture signals a symptomatology which may be attributed to Alzheimer's disease, or alternatively an increased probability in subjects of developing Alzheimer's disease relative to the population as a whole, the increase in probability being by a factor of at least 4.

The biological sample can be whole blood, the leucocyte fraction of blood or alternatively a tissue from which DNA may be extracted, or a biological fluid.

The specific primers used in the context of the present invention can be, in particular, those described in Roppers et al. (1991), Cytogenet. Cell Genet. 58, 751–784 for D19S178, Hixson et al. (1990), J. Lipid. Res. 31, 545–548 for APOE and Weber et al., Am. J. Hum. Genet. 44, 388–396 for APO CII.

Other primers may be suitable, the criterion for selection of primers being that they permit the amplification of the parts of the APOE, D19S178 and APO CII genes containing the respective polymorphisms: region 112–158 of APOE, 5' end of APO CII.

The alleles tested for, in particular D19S178 and long APO CII, may be demonstrated by determination of the length of the amplified fragments, for example by polyacrylamide gel electrophoresis, or by determination of the sequence of the amplified fragment.

The alleles tested for, in particular APO ε4, may also be detected by the technique of analysis of single-strand conformation polymorphism (SSCP), as described by Masato Orita et al., or alternatively by probe hybridization using a specific probe.

The subject of the present invention is also a kit for carrying out the method according to the invention, in a sample, comprising the following components:

pairs of specific primers for the APOE, D19S178 and APO CII genes, the reagents needed for performing a DNA amplification, where appropriate, the reagents permitting the detection of the APOE ε4, short D19S178 and/or long APO CII alleles, for example reagents needed for a polyacrylamide gel electrophoresis and the visualization of the fragments after migration, where appropriate, reference standards consisting of the wild-type alleles of the mutant genes.

The subject of the present invention is also amplification products of all or part of at least two genes selected from APOE, APO CII and D19S178.

It also relates to a diagnostic composition consisting of at least two genetic markers selected from APOE, APO CII and D19S178.

The results of the study of the inventors who are the authors of the present invention will be reported below, showing the involvement of the APOE, APO CII and D19S178 markers in the frequency of occurrence of Alzheimer's disease.

The study covered two groups of patients suffering from Alzheimer's disease, a French group composed of 36 patients suffering from a late onset form of Alzheimer's disease (78±9 years; range 65–91 years) and a British group composed of 34 patients exhibiting an early onset form of Alzheimer's disease (57±4 years; range 49–64 years), diagnosed on clinical criteria.

These two groups were compared with two control groups of the same origin and ages, composed of 38 and 36 subjects, respectively, whose environment was identical to that of the patients suffering from Alzheimer's disease.

The patients' genomic DNA was extracted from the leucocytes according to the method described by Marcadet et al. (Standardized Southern-Blot Workshop Technique-Histocompatibility Testing, Springer Verlag, New York, Vol. 1). The genomic DNA was amplified by PCR using a Perkin Elmer Cetus amplification apparatus.

Five markers localized in the chromosomal region 19q13.2 were studied as described in the corresponding references: two anonymous markers containing $(CA)_n$ motifs, D19S47 (reference under Mfd 9 (Weber et al. (1989), Am. J. Hum. Genet. 44, 388–396)) and D19S178 (referenced under Mfd 139 (Ropers et al. (1991) Cytogenet. Cell Genet. 58, 751–784)), the APOE polymorphism (Hixon et al. (1990) J. Lipid Res. 31, 545–548), the restriction fragment length polymorphism (RFLP) for HpaI of the 5' end of the APO CI gene locus (Nillesen et al. (1990), Nucleic Acids Res. 18, 3428) and the polymorphism of $(CA)_n$ repeat motifs in the APO CII gene (referenced under Mfd 5) (Weber et al., Am. J. Hum. Genet. 44, 388–396).

Statistical analyses were carried out with an SAS version 6.04 software package. "Univariate" analyses were carried out using Pearson's $\chi_2$ test and Fisher's exact test if necessary. In view of the rarity of the frequency of some alleles observed for microsatellite polymorphisms, the alleles were grouped together in two groups in accordance with their number of nucleotides. Thus, D19S178 was apportioned into long alleles (167 nucleotides and above) and short alleles (fewer than 167 nucleotides), and the alleles of the 5' end of APO CII having repeat motifs were divided into long alleles (30 repeat motifs and above) and short alleles (fewer than 30 repeat motifs).

Allelic frequencies were calculated by counting the alleles.

The results recorded were computer processed using a model of stepwise logistic regression by means of statistical tests of probability as described by Breslow N. E. et al., Statistical Methods in Cancer Research, Vol. 1, pp. 192–247. Analysis of the linkage disequilibria was carried out as described by Thompson E. A. et al., Am. J. Hum. Genet., 42, 113–124 and Hill, W. G., 1974, Hereditary, 33, 229–239.

The frequencies of D19S178, APOE, APO CI and APO CII markers were estimated using the algorithm described by McLean and Morton, Genet. Epidemiol. 2, 263–272, put into the form of a computer program, as described by Cox et al., Am. J. Hum. Genet., 43, 495–501.

Estimated frequencies were compared with those expected on the basis of the balance of Pearson's $\chi^2$ or of Fisher's exact test.

The results are reported in Tables I to IV below.

Table I reports the distributions of allelic frequency of the genomic polymorphisms for sporadic subjects suffering from Alzheimer's disease, relative to controls.

No significant difference is apparent between the subjects and the controls in the distribution of the D19S47 allele for the different populations. In the population with late onset of the disease, the frequencies of the polymorphisms of the APOE and APO CII genes were significantly different between the subjects and the controls: the APOE $\epsilon$4 allele and the long APO CII alleles were observed more frequently in the subjects with late onset Alzheimer's disease than in the controls.

The same analyses were carried out for an independent United Kingdom population of sporadic early onset subjects relative to controls. This population was studied for the two generally accepted limits of age at onset, namely less than 65 years and less than 60 years. For the group of subjects whose age at onset was under 65 years, the allelic distributions of the polymorphisms of the D19S178, APOE and APO CI genes were significantly different between the subjects and the controls: the short D19S178 alleles, the APOE $\epsilon$4 allele and the presence of the HpaI restriction site in APO CI (allele 2) were observed more frequently in patients in whom the onset of the disease was early than in the controls. For the groups of subjects with an age at onset of the disease of under 60 years, the allelic distributions of the polymorphisms of the D19S178, APOE and APO CI genes were similar to those of the group of subjects with an age at onset of the disease of under 65 years.

For the following analyses, the limit of separation in terms of age between the early onset group and the late onset group was 65 years.

The frequency observed for the APOE $\epsilon$4 allele in the early onset patient group was not significantly different from that observed in the late onset patient group and, in both populations, the APOE $\epsilon$2 allele was rare in subjects suffering from Alzheimer's disease.

An inverse correlation between the age at onset and the number of copies of the APOE $\epsilon$4 allele was observed in the late onset population (p<0.026) but not in the early onset population. The mean ages at onset of subjects having two APO $\epsilon$4 alleles, one $\epsilon$4 allele or no APO $\epsilon$4 allele were 70.5, 75.0 and 81.2 years, respectively, in the late onset group, and 58.5, 56.6 and 57.3 years, respectively, in the early onset group.

The results of studies of linkage disequilibrium in pairs between the D19S178, APOE, APO CI and APO CII polymorphisms are reported in Table II.

No deviation of the Hardy-Weinberg equilibrium was observed. A complete linkage disequilibrium was manifest between the APO $\epsilon$4 allele and allele 2 of the restriction fragment length polymorphism (RFLP) of APO CI in both populations.

In the control population, a non-significant linkage disequilibrium was manifest between the D19S178 and APOE polymorphisms and within the APOE-CI-CI'-CII assembly.

The haplotype frequencies of the 4 markers (D19S178, APOE, APO CI and APO CII) were estimated as reported in Table III below.

Among the 24 theoretical haplotypes, only 15 were to be found with the algorithm by the method described by McLean and Morton. Some haplotypes were observed only in the patients (Nos 1, 2 and 7) and others only in the controls (Nos 12 and 13), both in the late onset population and in the early onset population. The haplotype No. 10 was twice as frequent in the late onset patient population as in the early onset population.

The polymorphism information content (PIC) and the degree of heterozygosity obtained by combining these 4 markers were high in both groups.

The differences in the distribution of the estimated haplotype frequencies between the patients and the controls were tested by means of the likelihood ratio test with a number of degrees of freedom equal to 15. The results were 88.4 and 93.2, respectively, for the late onset patient group and the early onset patient group.

To estimate the tendency to develop the disease ("odds ratio") for the carriers of at least one of the alleles of the different genotypes, models of stepwise multiple logistic regression were used, which were adapted to the observations.

In the late onset group, the estimated odds ratios were 6.49 for the APOE $\epsilon$4 allele (95% confidence interval=[1.68; 25.03]), and 0.10 for the APOE 2 allele (95% confidence interval=[1.19; 10.70]).

In the early onset group, the estimated odds ratios obtained were 3.80 for the APO $\epsilon$4 allele (95% confidence interval=[0.01; 0.85]) and 4.44 for the short D19S178 alleles (95% confidence interval=[1.27; 15.49]).

The adjusted odds ratio (approximation of the risk) for the carriers of at least one APOE $\epsilon$4 allele of developing a sporadic early onset or late onset type Alzheimer's disease was 4.10 (95% confidence interval=[1.84; 9.16]), as estimated in a logistic regression model adapted for the data relating to the total population.

For the carriers of at least one APOE $\epsilon$2 allele, the odds ratio was 0.11 (95% confidence interval=[0.02; 0.50]), thus suggesting a protective effect of this allele.

The risk of developing an Alzheimer's disease for the carriers of at least one $\epsilon$4 allele and of at least one of the two markers, i.e. short D19S178 allele and long APO CII allele, is reported in Table IV below.

In both populations, the odds ratio risks were significantly increased when one of these two markers was considered at the same time as the APOE $\epsilon$4 allele.

For example, the risk of a late onset Alzheimer's disease manifesting itself for a subject carrying at least one APOE $\epsilon$4 allele and at least one long APO CII allele is maximal, this configuration never appearing in the controls. In this same late onset population, for the carriers of at least one APOE $\epsilon$4 allele and at least one short D19S178 allele, the odds ratio comes to 14 (14.23). These odds are also increased (greater than 8 (8.68)) for these same alleles in the case of an early onset Alzheimer's disease.

In the population as a whole, the risk of developing an Alzheimer's disease independently of the age at onset is increased for the carriers of at least one APOE $\epsilon$4 allele and at least one short D19S178 allele, as attested by the rise in the odds ratio to greater than 12 (12.46), as well as for the carriers of at least one APOE $\epsilon$4 and at least one long APO CII allele (odds ratio greater than 9 (9.72)).

TABLE I

Distribution of allelic frequency of genomic polymorphisms for subjects suffering from Alzheimer's disease relative to controls

| | D19S178 | | | APOE | | | APOCI | | | APOCII | | |
|---|---|---|---|---|---|---|---|---|---|---|---|---|
| | Allele° | A.D. | Controls | Allele | A.D. | Controls | Allele* | A.D. | Controls | Allele† | A.D. | Controls |
| Late onset age at onset ≧65 | n Short Long | 72 .43 .57 | 76 .38 .62 | n$ 2 3 4 | 72 .01 .75 .24 | 76 .15 .80 .05 | n 1 2 | 72 .71 .29 | 76 .79 .21 | n₊⁺ Short Long | 72 .62 .38 | 76 .78 .22 |
| Early onset age at onset <65 | n₊⁺ Short Long | 68 .57 .43 | 72 .40 .60 | n£ 2 3 4 | 68 .01 .70 .29 | 72 .14 .72 .14 | n₊⁺ 1 2 | 68 .56 .44 | 72 .72 .28 | n Short Long | 68 .75 .25 | 72 .75 .25 |
| Early onset age at onset <60 | n Short Long | 50 .56 .44 | 72 .40 .60 | n# 2 3 4 | 50 .02 .66 .32 | 72 .14 .72 .14 | n 1 2 | 50 .56 .44 | 72 .72 .28 | n Short Long | 50 .72 .28 | 72 .75 .25 |

A.D.: Subjects suffering from Alzheimer's disease
n = number of chromosomes
°= Polymorphism of (CA)$_n$ repeat units of D19S178
Short = number of nucleotides < 167;
Long = number of nucleotides ≧ 167
*APO CI Hpa restriction site
1 = absence of restriction site;
2 = presence of restriction site
†Polymorphism of APO CII (CA)$_n$ repeat units
Short = number of repeat units < 30;
Long = number of repeat units ≧ 30
A.D. against controls = ₊⁺p < .04;
p < .01;
£p < .004;
$p < .0001

TABLE II

Linkage disequilibria in pairs in the chromosomal region 19Q13.2

| Late onset subjects | D19S178 | APOE | APOCI | APOCII | Early onset controls | D19S178 | APOE | APOCI | APOCII |
|---|---|---|---|---|---|---|---|---|---|
| D19S178 | — | −.092 | −.069 | .040 | D19S178 | — | −.185 | −.067 | .160 |
| APOE 3 | 18.5 | — | 0.89* | .254 | APOE | 100.0 | — | .461* | −.122 |

TABLE II-continued

Linkage disequilibria in pairs in the chromosomal region 19Q13.2

| | | | | | | | | | |
|---|---|---|---|---|---|---|---|---|---|
| APOCI | 12.7 | 98.9 | — | .348 | APOCI | 16.3 | 100.0 | — | −.074 |
| APOCII | 3.7 | 33.9 | 42.3 | — | APOCII | 10.6 | 100.0 | 27.3 | — |

| Early onset subjects | D19S178 | APOE | APOCI | APOCII | Late onset controls | D19S178 | APOE | APOCI | APOCII |
|---|---|---|---|---|---|---|---|---|---|
| D19S178 | — | .171 | −.033 | .030 | D19S178 | — | −.141 | −.004 | −.046 |
| APOE | 13.0 | — | .726* | .114 | APOE | 42.9 | — | .648* | −.232 |
| APOCI | 4.3 | 100.0 | — | .050 | APOCI | 0.8 | 100.0 | — | −.178 |
| APOCII | 1.9 | 10.4 | 3.3 | — | APOCII | 9.6 | 100.0 | 48.6 | — |

APOE polymorphism analysed as biallelic marker (allele 4 against allele 2 or 3)
Above the diagonal Δ representing the standardized coefficient of linkage disequilibrium
Below the diagonal D' representing the percentage of the maximum coefficient of linkage disequilibrium of the possible values at the given allelic frequencies

TABLE III

Estimations of the haplotype polymorphism in the chromosomal region 19q13.2

| Number of haplotypes | Polymorphisms | | | | Estimated late onset | | Estimated early onset | | TOTAL estimated | | expected |
|---|---|---|---|---|---|---|---|---|---|---|---|
| | D19S178 | APOE | APOCI | APOCII | Subjects | Controls | Subjects | Controls | Subjects | Controls | Controls |
| 1 | S | 4 | 2 | L | .045 | .000 | .050 | .000 | .055 | .000 | .002 |
| 2 | L | 4 | 2 | L | .103 | .000 | .048 | .000 | .067 | .000 | .003 |
| 3 | S | 4 | 2 | S | .040 | .000 | .063 | .032 | .052 | .016 | .007 |
| 4 | L | 4 | 2 | S | .062 | .053 | .133 | .107 | .097 | .079 | .011 |
| 5 | S | 3 | 1 | L | .103 | .119 | .052 | .051 | .097 | .085 | .052 |
| 6 | S | 3 | 1 | S | .214 | .162 | .261 | .223 | .215 | .200 | .176 |
| 7 | S | 3 | 2 | L | .014 | .000 | .026 | .000 | .006 | .000 | .017 |
| 8 | S | 3 | 2 | S | .000 | .013 | .106 | .000 | .061 | .007 | .056 |
| 9 | L | 3 | 1 | L | .083 | .053 | .074 | .169 | .073 | .104 | .081 |
| 10 | L | 3 | 1 | S | .308 | .456 | .172 | .281 | .251 | .368 | .271 |
| 11 | L | 3 | 2 | L | .014 | .000 | .000 | .000 | .012 | .000 | .026 |
| 12 | L | 2 | 2 | L | .000 | .039 | .000 | .002 | .000 | .029 | .005 |
| 13 | L | 2 | 2 | S | .000 | .018 | .000 | .039 | .000 | .029 | .016 |
| 14 | S | 2 | 2 | L | .014 | .000 | .000 | .029 | .004 | .012 | .003 |
| 15 | S | 2 | 2 | S | .000 | .088 | .015 | .069 | .010 | .072 | .010 |
| H | | | | | .82 | .74 | .87 | .82 | .85 | .79 | |
| PIC | | | | | .80 | .71 | .86 | .80 | .84 | .77 | |
| Number of chromosomes | | | | | 72 | 76 | 68 | 72 | 140 | 148 | |

H = Degree of heterozygosity;
PIC = Polymorphism Information Content
The expected frequencies were calculated for controls exhibiting the corresponding product at the allelic frequencies for each polymorphism.
Differences between the estimated haplotype frequencies and the expected haplotype frequencies, assuming an equilibrium of the linkages (p < 0.01).

TABLE IV

Estimation of the "odds ratio" for subjects having at least one ε4 allele with polymorphism of the short D19S178 allele or polymorphism of the long APO CII allele

| | | Alzheimer's disease | Controls | "Odds ratio" | p |
|---|---|---|---|---|---|
| Late onset | n | 36 | 38 | | |
| | With at least 1 short D19S178 allele | .28 | .03 | 14.23 | <.002 |
| | With at least 1 long APOCII allele | .31 | .00 | ∞ | <.0002 |
| Early onset | n | 34 | 36 | | |
| | With at least 1 short D19S178 allele | .44 | .08 | 8.68 | <.0006 |
| | With at least 1 long APOCII allele | .21 | .06 | 4.41 | <.06 |

TABLE IV-continued

Estimation of the "odds ratio" for subjects having at least one ε4 allele with polymorphism of the short D19S178 allele or polymorphism of the long APO CII allele

| | | Alzheimer's disease | Controls | "Odds ratio" | p |
|---|---|---|---|---|---|
| Total | n | 70 | 74 | | |
| | With at least 1 short D19S178 allele | .26 | .03 | 12.46 | <.0001 |
| | With at least 1 long APOCII allele | .36 | .05 | 9.72 | <.00001 |

We claim:

1. A method of predicting an increased risk of a patient having Alzheimer's disease or developing Alzheimer's disease, comprising:

amplifying the DNA in a DNA-containing biological sample from a patient with a first pair of primers and a second pair of primers which amplify (1) at least a portion of the APOE gene and at least a portion of the APO CII gene, respectively, or (2) at least a portion of the APOE gene and at least a portion of the D19S178 gene, respectively; and assaying for the presence of (1) the APOE ε4 allele and the long APO CII allele or (2) the APOE ε4 allele and the short D19S178 allele, wherein the presence of (1) the APOE ε4 allele and the long APO CII allele or (2) the APOE ε4 allele and the short D19S178 allele indicates an increased risk for the patient having Alzheimer's disease or developing Alzheimer's disease.

2. The method of claim 1, wherein the first pair of primers and the second pair of primers amplify at least a portion of the APOE gene and at least a portion of the APO CII gene, respectively, and said method comprises assaying for the presence of the APOE ε4 allele and the long APO CII allele in the assaying step.

3. The method of claim 1, wherein the first pair of primers and the second pair of primers amplify at least a portion of the APOE gene and at least a portion of the D19S178 gene, respectively, and said method comprises assaying for the presence of the APOE ε4 allele and the short D19S178 allele in the assaying step.

4. The method of claim 1, wherein the short D19S178 allele contains fewer than 167±4 nucleotides.

5. The method of claim 4, wherein the short D19S178 allele contains fewer than 167 nucleotides.

6. The method of claim 1, wherein the long APO CII allele contains more than 30±3 cytosine-adenine repeat motifs.

7. The method of claim 6, wherein the long APO CII allele contains more than 30 cytosine-adenine repeat motifs.

8. The method of claim 1, wherein the DNA in the sample is rendered accessible to hybridization with the primers prior to the amplifying step.

9. The method of claim 1, wherein the DNA in the sample is amplified by the polymerase chain reaction (PCR).

10. The method of claim 1, wherein the presence of said alleles is assayed by polyacrylamide gel electrophoresis.

11. The method of claim 1, wherein at least region 112–158 of the APOE gene is amplified in the amplifying step.

12. The method of claim 1, wherein at least the 5' end of the APO CII gene is amplified in the amplifying step.

13. A method of predicting an increased risk of a patient having Alzheimer's disease or developing Alzheimer's disease, comprising:

amplifying the DNA in a DNA-containing biological sample from a patient with a first pair of primers which amplify at least a portion of the APOE gene, a second pair of primers which amplify at least a portion of the APO CII gene, and a third pair of primers which amplify at least a portion of the D19S178 gene; and assaying for the presence of the APOE ε4 allele, the long APO CII allele, and the short D19S178 allele, wherein the presence of the APOE ε4 allele, the long APO CII allele, and the short D19S178 allele indicates an increased risk for the patient having Alzheimer's disease or developing Alzheimer's disease.

14. The method of claim 13, wherein the short D19S178 allele contains fewer than 167±4 nucleotides.

15. The method of claim 13, wherein the short D19S178 allele contains fewer than 167 nucleotides.

16. The method of claim 13, wherein the long APO CII allele contains more than 30±3 cytosine-adenine repeat motifs.

17. The method of claim 13, wherein the DNA in the sample is rendered accessible to hybridization with the primers prior to the amplifying step.

18. The method of claim 13, wherein the DNA in the sample is amplified by the polymerase chain reaction (PCR).

19. The method of claim 13, wherein the presence of said alleles is assayed by polyacrylamide gel electrophoresis.

20. The method of claim 13, wherein at least region 112–158 of the APOE gene is amplified in the amplifying step.

21. The method of claim 13, wherein at least the 5' end of the APO CII gene is amplified in the amplifying step.

22. A kit, comprising:

a first pair of primers and a second pair primers which are capable of amplifying (1) at least a portion of the APOE gene and at least a portion of the APO CII gene, respectively, or (2) at least a portion of the APOE gene and at least a portion of the D19S178 gene, respectively;

a first reagent and a second reagent for assaying for the presence in a DNA sample of (1) the APOE ε4 allele and the long APO CII allele, respectively, or (2) the APOE ε4 allele and the short D19S178 allele, respectively, wherein the first reagent and the second reagent are each a probe specific for the respective allele.

23. The kit of claim 22, wherein the first pair of primers and the second pair primers are capable of amplifying at least a portion of the APOE gene and at least a portion of the APO CII gene, respectively, and the kit further comprises a third pair of primers which is capable of amplifying at least a portion of the D19S178 gene.

24. The kit of claim 22, wherein the first pair of primers and the second pair primers are capable of amplifying at least a portion of the APOE gene and at least a portion of the D19S178 gene, respectively, and the kit further comprises a third pair of primers which is capable of amplifying at least a portion of the APO CII gene.

25. The kit of claim 22, further comprising at least one reagent for amplifying DNA.

26. The kit of claim 22, further comprising at least one reagent for performing polyacrylamide gel electrophoresis.

* * * * *